United States Patent [19]

Heindel et al.

[11] Patent Number: 4,949,668
[45] Date of Patent: Aug. 21, 1990

[54] APPARATUS FOR SPRAYED ADHESIVE DIAPER CONSTRUCTION

[75] Inventors: Timothy R. Heindel, Neenah, Wis.; Michael J. Garvey, Cordova, Tenn.; Daniel W. Dick, Paris, Tex.; Richard F. Keller, Hortonville, Wis.; Mary P. Jordan, Neenah, Wis.; Alan F. Schleinz, Appleton, Wis.

[73] Assignee: Kimberly-Clark Corporation, Neenah, Wis.

[21] Appl. No.: 207,682

[22] Filed: Jun. 16, 1988

[51] Int. Cl.$^5$ .............................................. B05B 13/02
[52] U.S. Cl. ...................................... 118/314; 118/324
[58] Field of Search ............... 118/302, 312, 313, 314, 118/315, 324; 425/90, 96, 97, 101, 102

[56] References Cited

U.S. PATENT DOCUMENTS

| | | | |
|---|---|---|---|
| 2,571,457 | 10/1951 | Ladisch | 18/54 |
| 2,903,387 | 9/1959 | Wade | 154/101 |
| 2,950,752 | 8/1960 | Watson et al. | 154/1 |
| 2,988,469 | 6/1961 | Watson | 154/101 |
| 3,017,664 | 1/1962 | Ladisch | 18/2.5 |
| 3,523,536 | 8/1970 | Ruffo | 128/287 |
| 3,543,332 | 12/1970 | Wagner et al. | 18/8 |
| 3,796,617 | 3/1974 | Wiltshire | 156/62.2 |
| 3,833,698 | 9/1974 | Wiltshire | 264/91 |
| 3,904,339 | 9/1975 | Dunn | 425/162 |
| 3,905,734 | 9/1975 | Blair | 425/224 |
| 3,911,173 | 10/1975 | Sprague | 427/207 |
| 4,118,531 | 10/1978 | Hauser | 428/224 |
| 4,185,981 | 1/1980 | Ohsato et al. | 65/5 |
| 4,478,624 | 10/1984 | Battigelli et al. | 65/4.4 |
| 4,573,986 | 3/1986 | Minetola et al. | 604/366 |
| 4,815,660 | 3/1989 | Boger | 118/302 |
| 4,842,666 | 6/1989 | Werenicz | 156/161 |

FOREIGN PATENT DOCUMENTS

WO83/04040  11/1983  World Int. Prop. O. .......... 118/302

OTHER PUBLICATIONS

"Application Potential of Controlled Fiberization Spray Technology", Nonwovens Industry, Jan. 1988, p. 44-46.
[Advertisement], Nonwovens Industry, May 1988, pp. 46-49.
Publication: Adhesive Age; Title: Three Steps in the Evolution HMPSA Spray Technology; Author: John Raterman; Date: Nov. 1987.

Primary Examiner—Bernard Nozick
Attorney, Agent, or Firm—Paul Yee

[57] ABSTRACT

A distinctive method and apparatus for depositing a pattern of material, such as hot-melt adhesive, onto a substrate comprises a supplying mechanism for forming a first and at least a second substantially continuous stream of the selected material, and a gas-directing mechanism for forming a plurality of gas streams. The gas streams have selected velocities and are arranged to entrain the material streams to impart a swirling motion to each of the material streams as it moves toward the substrate. A transport mechanism moves the substrate relative to the supply mechanism along a selected machine direction. A regulating mechanism controls the supplying mechanism and gas-directing mechanism to direct the material stream in a selected path toward the substrate and deposit the material in adjacent semi-cycloidal patterns on the substrate while closely controlling a selected cross-directional positioning of one or more of the deposited patterns.

29 Claims, 8 Drawing Sheets

FIG. IA

APPARATUS FOR SPRAYED ADHESIVE DIAPER CONSTRUCTION

FIELD OF INVENTION

The present invention relates to a method and apparatus for applying a selected pattern of liquid material onto a chosen substrate. More particularly, the present invention relates to a method and apparatus for spraying a selected pattern of hot-melt adhesive onto a moving substrate layer to construct a garment article, such as a disposable diaper.

BACKGROUND OF INVENTION

In the manufacture of disposable absorbent articles, such as diapers, feminine care products, incontinence products, and the like, adhesives have typically been applied in a pattern of multiple, parallel glue lines which extend along the longitudinal dimension of the article. Such glue line patterns leave unbonded gaps between the lines, and the unbonded gap areas tend to have lower strength and lower integrity. As a result, the article can be more susceptible to stretching and tearing when adhesive tapes are employed to secure the article on the wearer, and the article may be less able to maintain its structure and hold together during use.

Sprayed and foamed adhesives have also been employed to assemble together various component layers of disposable absorbent articles. The adhesives may be thermoplastic-type adhesives or solvent-type adhesives. For example, see U.S. Pat. No. 3,523,536 to A. Ruffo and U.S. Pat. No. 4,118,531 to Minetola, et al. Swirled patterns of adhesive have been employed to construct articles such as shoes. For example, see U.S. Pat. No. 3,911,173 issued Oct. 7, 1975 to J. Sprague.

Various air forming techniques have been employed to form nonwoven fibrous webs. For example, U.S. Pat. No. 4,478,624 issued Oct. 23, 1984 to J. Battigelli, et al. describes a technique which employs a circular airflow component to help produce a more uniform distribution of fibers laid onto a foraminous conveyor. U.S. Pat. No. 2,903,387 issued Sept. 8, 1959 to W. Wade describes a technique for producing reticulated fibrous webs containing tubular or hollow fibers of elastomeric material. U.S. Pat. No. 2,950,752 issued Aug. 30, 1960 to P. Watson, et al. describes a spraying technique for forming relatively long, discontinuous, fine fibers of elastomeric materials. The fiber-forming liquid is extruded into and within a primary or high velocity stream of gas as a stream of plastic which is broken transversely into a plurality of fibers or fibrils before landing on a collector. U.S. Pat. No. 2,988,469 issued June 13, 1961 to P. Watson describes a further spraying technique for forming relatively long, discontinuous, fine fibers of nonelastomeric material. A high velocity jet stream of gas attenuates and fibrillates a single large-diameter plastic stream into a multiplicity of fibers and fibrils without the formation of shot.

Molded articles and preforms have been produced by depositing fibers into a form and binding the fibers together with a resin binder. For example, U.S. Pat. No. 3,796,617 issued Mar. 12, 1974 to A. Wiltshire describes a method for making a fibrous preform which comprises the steps of randomly depositing short reinforcing fibers on a form, binding the fibers together with a settable resin binder, and rolling the resin-coated fibers on the form into a dimensionally uniform porous mat. U.S. Pat. No. 3,833,698 describes a technique in which chopped fibers are directly deposited in a localized manner onto the interior surface of a screen form. The fibers are held in place by an airflow through the screen form into a vacuum chamber, and the deposited chopped fibers are sprayed with a heat-curable resin binder. U.S. Pat. No. 3,904,339 issued Sept. 9, 1975 to J. Dunn describes a technique for depositing glass fibers and curable resin into molds. A spray means for depositing the resin and fibers is supported on an arm which is pivoted about a selected axis.

Particular nozzle structures have been developed to form filaments from thermoplastic, melt-extrudable materials. The nozzles may be configured to produce a swirling air flow which disrupts the flow of extruded material into a plurality of fine fibers. For example, U.S. Pat. No. 4,185,981 describes a technique for producing fibers from a viscous melt. High-speed gas streams have a component in the tangential direction of the circular sectional surface of the melt, and a component which approaches the central axial line of the melt towards the flowing direction of the melt and then departs from the central axial line. The melt is continuously flown as fiber in the flowing direction and outwardly in the radial direction in a vortex form, which is spiral or helical or both. The fibrous melt which has flown away is accelerated and drawn into long fibers having a diameter of 10-100 microns, or short fibers having a diameter of 0.1-20 microns. The fibers can then be accumulated to form a fibrous mat.

U.S. Pat. No. 2,571,457 issued Oct. 16, 1951 to R. Ladisch describes a technique in which a cyclone of gas disrupts a "filament forming liquid" into fibers and/or filaments which may be collected on a moving belt. U.S. Pat. No. 3,017,664 issued Jan. 23, 1962 to R. Ladisch describes a fiber-forming nozzle wherein a fiber-forming liquid is spread over the outside wall of a circular body as a thin film, and wherein a stream of spiraling elastic fluid rotates at high velocity to draw out fibers which are picked up from the film of fiber-forming liquid.

U.S. Pat. No. 3,905,734 issued Sept. 16, 1975 to E. Blair describes an apparatus for continuously making a tube of meltblown microfibers. The meltblown microfibers are deposited longitudinally upon a circumferential surface of a mandrel and then are axially withdrawn from one end of the mandrel tube.

U.S. Pat. No. 3,543,332 issued Dec. 1, 1970 to W. Wagner, et al. describes a spinning nozzle for spray spinning molten fiber-forming materials and forming fibrous assemblies such as nonwoven fabrics and the like. The nozzle includes gas passages which are inclined so that their axes do not intersect the axis of an extrusion orifice in the nozzle. Gas streams act to swirl filaments formed from the fiber-forming material to produce a random expanding conical pattern as the filaments travel toward a moving collector.

An article entitled "*Application Potential of Controlled Fiberization Spray Technology*" Nonwovens Industry, January 1988 by J. Raterman describes a process for spraying pressure-sensitive hot-melts. The process employs a line of spray heads using nozzles with integral air jets that produce fine monofilaments of adhesive swirled at high speeds in a helix or spiral pattern.

Conventional spray techniques, such as those discussed above, have not adequately regulated the distribution pattern and placements of the sprayed material onto a substrate. Ordinarily, the sprayed materials are deposited in a generally random pattern, and there can be excessive overspray and misplacement of the deposited materials. Where the sprayed materials are composed of adhesives, such as hot-melt adhesives, the overspray and misplacement can contaminate the equipment and require excessive maintenance. For the purpose of applying adhesives onto a substrate, the conventional techniques have not provided a sufficiently accurate control over the deposition pattern and have not been sufficiently flexible or readily adjustable to accommodate the placement of adhesives onto different widths of substrate. In addition, the conventional spray devices have been excessively sensitive to plugging when employed with viscous liquids, such as hot-melt adhesives.

BRIEF DESCRIPTION OF THE INVENTION

The present invention provides a distinctive apparatus for depositing a pattern of material onto a substrate. Generally stated, the apparatus includes supplying means for forming a first and at least a second stream of a selected material, and gas directing means for forming a plurality of gas streams. The gas streams have selected velocities and are arranged to entrain the material streams to impart a swirling motion to each of the material streams as it moves toward the substrate. Transport means move the substrate relative to the supplying means along a selected machine direction. Regulating means control the supplying means and the gas directing means to direct each of the entrained material streams in a selected path toward the moving substrate and deposit the material thereon to form adjacent semi-cycloidal patterns of the material on the substrate while closely controlling a cross-directional positioning of one or more of the patterns.

The invention further provides a method for depositing a selected pattern of material onto a substrate. Generally stated, the method includes the steps of supplying a first and at least a second stream of a selected material, and forming a plurality of gas streams which have selected velocities and are arranged to entrain the material streams to impart a swirling motion to each of the material streams as it moves toward the substrate. The substrate is moved relative to the supplying means along a selected machine direction, and the material and gas streams are controlled to direct the entrained material stream in a selected path toward the substrate and deposit the material thereon to form a semi-cycloidal pattern of the material on the substrate while closely regulating a cross-directional positioning of one or more of the patterns.

In addition, the invention can provide a distinctive absorbent article comprising an outer layer, a liquid-permeable inner layer, and an absorbent body positioned between the inner and outer layers. A pattern of adhesive is arranged to secure one or more of the layers to the absorbent body, and is composed of a plurality of juxtaposed, substantially continuous, semi-cycloidal arrays of adhesive extending substantially along a longitudinal dimension of the article.

The method and apparatus of the present invention can advantageously provide a more accurate placement of deposited material onto a substrate layer, and can provide a more precise formation of a desired deposition pattern. Since the molten adhesive is gas-entrained for a discrete distance before contacting the substrate web, the adhesive has an opportunity to cool, or depending on the temperature of the gas, may be held or maintained at a selected temperature. The cooling reduces the probability that the web will be exposed to excessive amounts of heat from the adhesive. The technique of the present invention can be readily adjustable to accommodate and control the placement of material onto substrates of various widths. The technique of the invention can also reduce the amount of overspray waste and reduce the maintenance requirements for the associated production equipment. In addition, the invention can provide a more effective distribution of adhesive on the applied surface area of the article, and can thereby provide an article having more uniform strength characteristics. An article constructed in accordance with the invention may be perceived by the consumer as having increased integrity.

BRIEF DESCRIPTION OF THE DRAWINGS

The invention will be more fully understood and further advantages will become apparent when reference is made to the following detailed description of the invention and the drawings, in which.

DETAILED DESCRIPTION OF THE INVENTION

The present invention provides a distinctive method and apparatus for depositing a selected pattern of material onto a selected substrate, such as the outer cover layer of a disposable diaper. While the following description will be made in the context of depositing a hot-melt adhesive, it will be readily apparent to persons of ordinary skill that other types of adhesives and other types of viscous, extrudable materials may also be applied by employing the technique of the invention. Similarly, while the following description will be made in the context of constructing a disposable diaper, it will be readily apparent that the technique of the present invention would also be suitable for producing other articles, such as feminine care products, incontinence products, disposable gowns, laminated webs, and the like.

Figure 1:
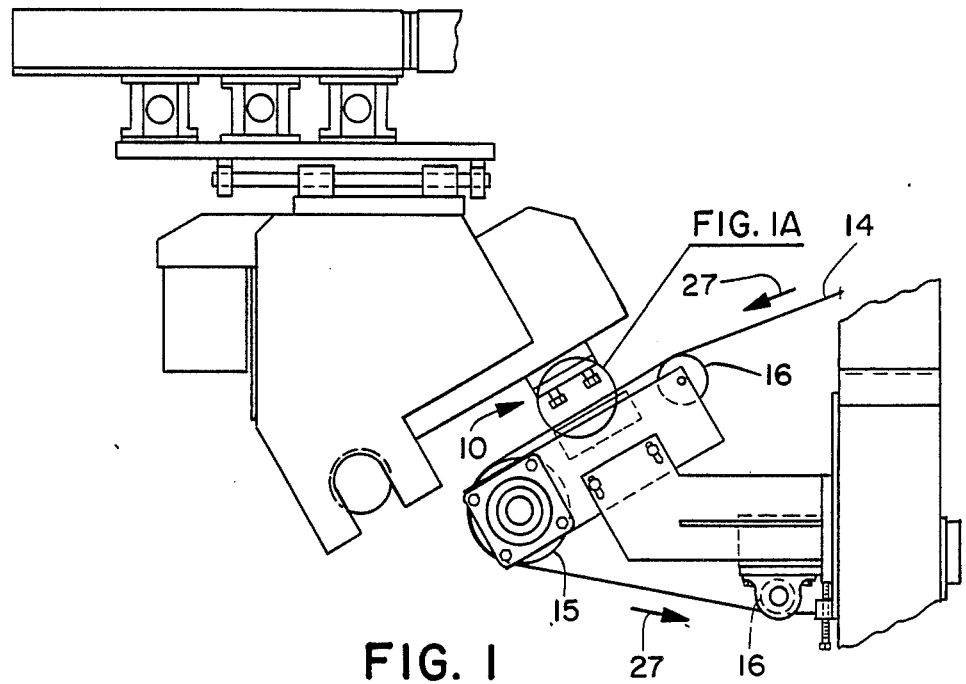
FIG. 1 representatively shows a side elevational view of the apparatus of the present invention.
Figure 1A:
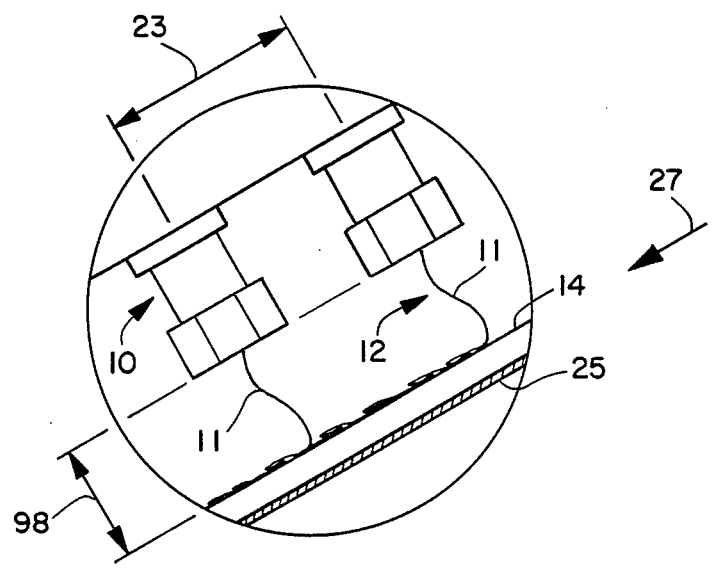
FIG. 1A representatively shows an enlarged view of the region circled in FIG. 1.

With reference to FIGS. 1 and 1A, an apparatus for depositing a pattern of selected material, such as hot-melt adhesive 12, onto a substrate, such as web 14. The apparatus includes a supply means, such as nozzle assembly 10, for forming at least one, substantially continuous stream of the material. Gas directing means, such as gas jets 30 (FIG. 2), form at least one gas stream, which has a selected velocity and is arranged to entrain the material stream 11 to impart a swirling motion to the material stream as it moves toward substrate web 14. Transport means, such as conveyor rollers 15 and 16, move the substrate relative to the supplying means along a selected machine direction 27 (substrate movement direction). Regulating means, including pumps 33 (FIG. 8) and pressure control valve 18 (FIG. 9), control the material stream and the velocity of the gas stream, respectively, to direct material stream 11 in a selected path toward substrate 14 and deposit the material thereon to form a substantially continuous, semi-cycloidal pattern of the material on substrate 14.

Roller 15 may optionally be a constant temperature roll which is held at a temperature below or above the ambient temperature, as desired. As a result, roller 15 can operably support and guide web 14 and can also operably cool or heat the web. For example, roller 15 may be a chill roll which is conventionally configured with a plurality of internal passages, and constructed and arranged to conduct and transport a suitable liquid coolant therethrough. The coolant can be cooled by a conventional refrigeration unit to a temperature of about 18° C., and the circulation of the coolant through the chill roll operably maintains the outer surface of the chill roll at a predetermined temperature. The resultant cooling action provided by chill roll 15 helps prevent excessive heating of web 14 by the hot-melt adhesive deposited thereon, and can accelerate the solidification of the adhesive on the web.

A drip plate 25 is located below the position occupied by web 14 as the web moves over the conveyor rollers and past the location of nozzle assembly 10. The drip plate is constructed and arranged to intercept and catch any excess hot-melt adhesive which might be expelled or drip from the nozzle units 24 during any time that web 14 is absent from the system. The presence of drip plate 25 can thereby advantageously reduce the contamination of the equipment by fugitive adhesive, and reduce the amount of system maintenance. In particular, the presence of drip plate 25 can also prevent excessive equipment contamination during web splicing operations. In the shown embodiment, the drip plate is removable for cleaning.

Figure 2:
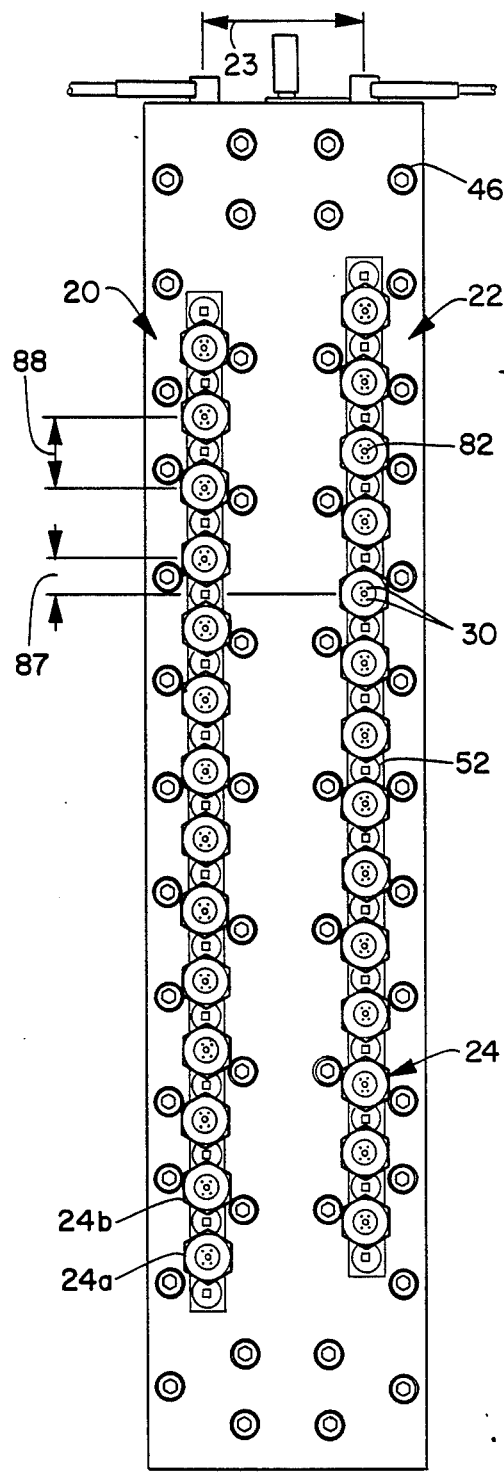
FIG. 2 representatively shows a plan view of an assembly comprising two nozzle banks.
Figure 3:
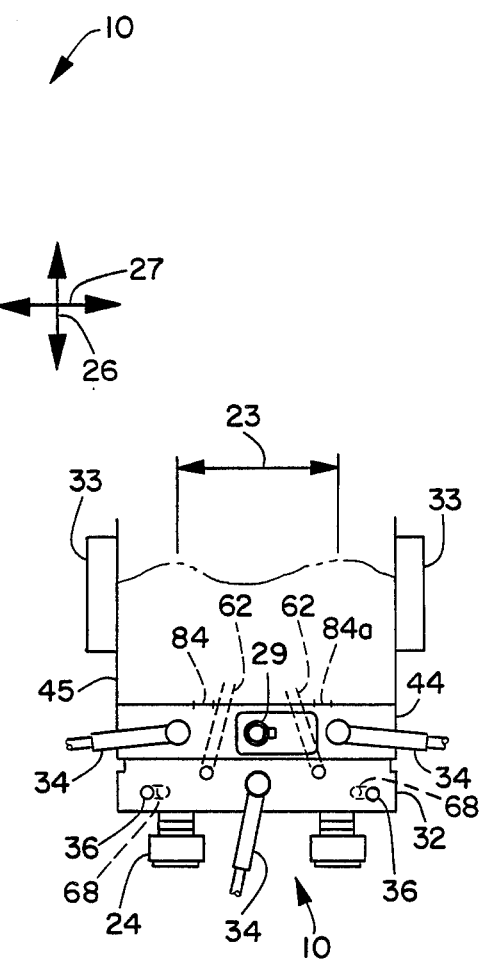
FIG. 3 representatively shows a side elevational view of the assembly illustrated in FIG. 2.

With reference to FIGS. 2 and 3, nozzle assembly 10 includes a first nozzle bank 20 and at least a second nozzle bank 22, with the first nozzle bank spaced a selected offset distance 23 from the second nozzle bank along machine direction 27 of the apparatus. The offset distance is arranged and configured to substantially prevent interference between the deposition patterns formed by each of the individual nozzle units 24. Each nozzle bank 20, 22 includes a plurality of spaced-apart nozzle units 24 which are substantially aligned along a cross-direction 26 of the apparatus. The nozzles of first nozzle bank 20 are, however, positioned in an interposed, staggered arrangement relative to the nozzles of second nozzle bank 22. Each nozzle includes an orifice 82 for forming a stream of hot-melt adhesive 11, and includes a group of gas jets 30 for forming a particularly configured group of gas streams which have selected velocities and are arranged to entrain the associated, individual stream of hot-melt adhesive 11 issuing from orifice 82 to thereby impart a swirling motion to each material stream 11 as it moves toward web 14. In the illustrated embodiment, the individual nozzle units 24 within a particular nozzle bank are substantially equally spaced along the cross-direction. Alternatively, the individual nozzle units within a nozzle bank may be unequally spaced, if desired.

FIG. 3 representatively shows a nozzle assembly 10 comprising nozzle plate 32 and transfer plate 44 which are joined and held together with suitable fastening means, such as bolts 46. The nozzle plate and transfer plate are formed of a suitable material, such as metal. In the illustrated embodiment, the nozzle and transfer plates are composed of heat treated stainless steel. A suitable gas, such as air, is introduced into nozzle plate 32 through one or more gas inlets 36. In the illustrated embodiment, there are two individual gas inlets, but more or fewer inlets could also be employed. A desired liquid, such as hot-melt adhesive, which is to be applied to web 14, is provided into transfer plate 44 through liquid inlets 84 and 84a. In the illustrated embodiment, liquid inlets 84 supply molten adhesive to nozzles in first nozzle bank 20, and liquid inlets 84a supply molten adhesive to nozzles in second nozzle bank 22. Each individual nozzle unit receives adhesive supplied through an individual inlet. Excess liquid, which is not expelled through nozzle units 24, is recirculated out from nozzle plate 32, as discussed in more detail below with respect to FIG. 8. The recirculation of excess hot-melt adhesive can advantageously provide improved control over the deposition patterns of adhesive onto web 14 and can facilitate changes in the system to increase or decrease the total cross-directional width of web 14 which is covered by the array of adhesive deposition patterns.

Figure 4:
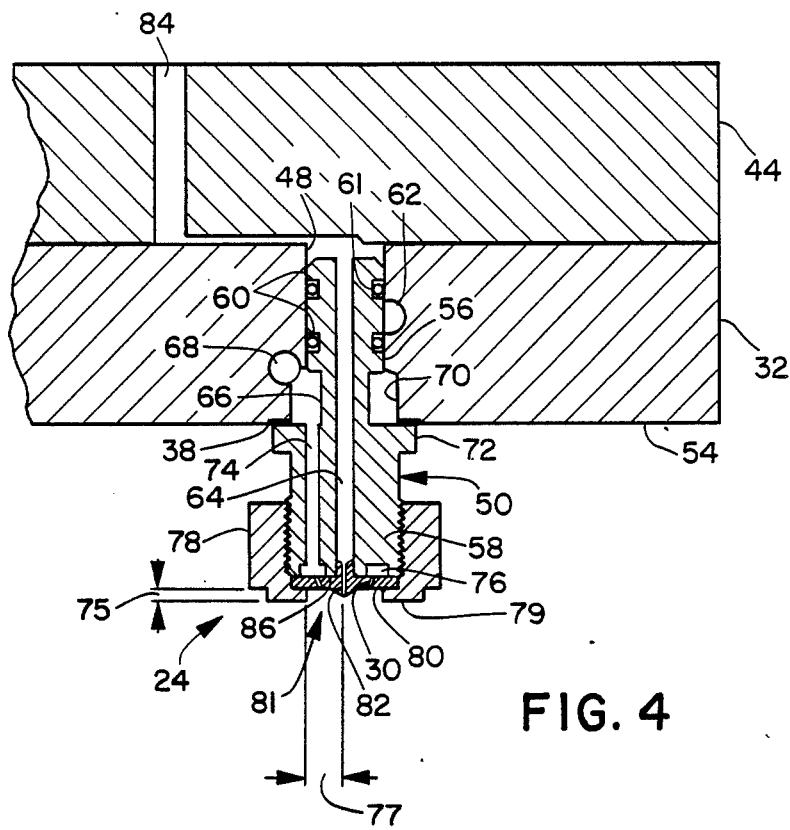
FIG. 4 representatively shows a cross-sectional view of an individual nozzle mechanism.

A more detailed illustration of a representative, individual nozzle unit 24 is representatively shown in FIG. 4. In the illustrated embodiment, nozzle plate 32 is configured with a plurality of nozzle bore holes 48 which extend through the thickness dimension of the nozzle plate and are suitably positioned in spaced arrangement corresponding to the desired locations of the individual nozzle units. Each bore hole 48 has an expanded region 70 of increased diameter located adjacent to one major surface 54 of nozzle plate 32. As a result, the nozzle bore has a stepped cross-sectional configuration.

Each bore hole 48 is constructed to receive therein a nozzle body 50 which is secured with suitable fastening means, such as bolts 52 (FIG. 2). The nozzle body is constructed of a suitable material, such as metal or high-strength, temperature-resistant plastic. In the illustrated embodiment, the nozzle body is composed of hardened stainless steel.

Nozzle body 50 includes a stem portion 56 and a head portion 58, and has an adhesive supply passage 64 formed axially therethrough. Stem portion 56 includes two circumferential grooves 60 configured to accommodate the placement of O-ring type seals composed of a conventional, high temperature elastomeric material, such as Viton type O-rings, which are produced by Parker Hannifin, a company having facilities in Lexington, Ky. Grooves 60 extend circumferentially around stem portion 56, and are constructed and arranged to hold the O-rings in sealing engagement with the interior wall surface of bore 48. In addition, grooves 60 are axially spaced along the length of stem portion 56, and are arranged to bracket either side of adhesive return port 62, which is formed through nozzle plate 32 in fluid communication with bore 48. In the illustrated embodiment, stem portion 56 is necked down with a reduced diameter at its medial section 66. The medial section cooperates with expanded region 70 of bore 48 to provide an annular passageway between the nozzle stem and the side wall of the bore hole. A gas inlet port 68 is formed through nozzle plate 32 and positioned in fluid communication with expanded region 70 of bore 48. Gasket member 38 provides a substantially airtight seal between surface 54 and flange 72. The gasket is composed of a conventional fibrous gasket material, and is configured to reduce air leaks caused by irregularities in the mating surfaces arising from manufacturing machining tolerances.

The head portion 58 of nozzle body 50 includes an annular flange 72 which extends about the head portion and is constructed to seat in engagement with the outer surface 54 of nozzle plate 32. The head portion further includes a gas passage 74, which is formed through the head portion. Gas passage 74 extends axially through the nozzle body head portion 58 and is radially spaced from adhesive supply passage 64. The gas passage is constructed and arranged to be in fluid communication with expanded region 70 of bore 48. In the illustrated embodiment, the distal, terminal end of head portion 58 includes an annular groove 76 which is formed into an axial end face 86 thereof. Groove 76 is configured to connect in fluid communication with gas passage 74. Union nut 8 secures head button 80 to the end face of head portion 58. The representatively shown embodiment of head button 80 is a generally circular, contoured disk which has an axially extending orifice passage 82 formed substantially through its center. Orifice passage 82 is configured to connect in fluid communication with supply passage 64, and the inwardly facing surface of head button 80 seats in sealing engagement with end face 86 of nozzle head portion 58. To produce a desired pattern of deposited material, orifice passage 82 is configured with a diameter of about 0.0305-0.0762 cm. (about 0.012-0.030 in.). Preferably, the diameter of orifice passage 82 is about 0.0457-0.0635 cm. (about 0.018-0.025 in.), and more preferably the diameter is about 0.0508 cm. to provide improved performance.

Head button 80 further includes gas jet passages 30 which are formed through the axial, thickness dimension of the head button. In the illustrated embodiment, four jet passages are radially spaced from orifice passage 82, and are circumferentially spaced at substantially equal intervals along a circle around the orifice passage. Each gas jet 30 is in fluid communication with annular groove 76, and is configured to direct an individual stream of gas from groove 76 into the ambient atmosphere surrounding the outlet of orifice passage 82. More particularly, each gas jet is constructed and arranged to produce a gas stream having both an axial velocity component as well as a circumferential velocity component. While the illustrated embodiment includes four gas jets 30, it is readily apparent that fewer or more than four gas jets may optionally be employed.

For the purposes of the present discussion, the axial direction is along the axis of nozzle body 50, and in particular, is along the direction defined by orifice passage 82. The circumferential direction is perpendicular to the axial direction and substantially tangential to the cylindrical surface delimited by nozzle body 50.

The shown embodiment of the invention employs gas jet passages which are inclined at a selected angle relative to the longitudinal axis of nozzle body 50 to thereby impart a circumferential velocity component to the gas stream expelled from nozzle jet 30. As a result, the collection of gas streams grouped around orifice 82 cooperate to entrain the stream of hot-melt adhesive issuing forth from orifice 82 and to impart a generally circular, swirling motion to the molten adhesive stream after the adhesive has exited from the orifice. In a particular aspect of the invention, the gas jets 30 are inclined circumferentially at an angle of about 30-55° relative to the axial dimension of the nozzle body and directed along substantially helical paths about the axial dimension. Preferably, the nozzle jets are inclined at an angle of about 40-50°, and more preferably are inclined at an angle of about 45° to provide improved performance.

In a particular aspect of the invention, the angled gas jets 30 and the supplied air pressure are configured and arranged to entrain the stream of hot-melt adhesive and impart at least about 300 swirls per second. Preferably, the invention imparts about 400-600 swirls per second to the adhesive stream, and more preferably, the invention imparts about 500 swirls per second to provide improved control of the adhesive deposition pattern.

A suitable head button component having the desired orifice and gas jet configurations is a Nordson nozzle part number 860435. This part is manufactured by Nordson Corp., a company having facilities in Norcross, Ga.

Union nut 78 engages threads formed on the outer surface of head portion 58 and operably clamps against the circumferential edges and outer surface of head button 80 to hold the head button onto the nozzle body. As illustrated in FIG. 4, the clamping portion of union nut 78 comprises an annular flange member 79 which contacts the outwardly facing surface of head button 80 along a circumferential edge section thereof. Flange member 79 extends radially inward toward orifice 82 and terminates at a position which is spaced from orifice 82 by a selected radial distance 77. In the shown embodiment, this flange spacing is within the range of about 0.3-0.5 cm., and preferably is about 0.4 cm. Flange member 79 also extends longitudinally along the axial dimension of the nozzle body by a selected distance 75, which in the shown embodiment is within the range of about 0.5-0.11 cm., and preferably is about 0.081 cm. As a result, flange member 79 delimits a substantially cylindrical chamber 81 into which gas jets 30 and orifice passage 82 exit. The chamber has a radius 77 and length 75.

It has been found that various factors can affect the diameter of the deposition pattern. Such factors include, for example, the air-to-adhesive ratio, the adhesive viscosity and the distance between nozzle head button 80 and web 14. Accordingly, it is contemplated that some adjustments to the system will need to be made depending upon the physical properties of the adhesive or other material being deposited onto web 14.

Figure 7:
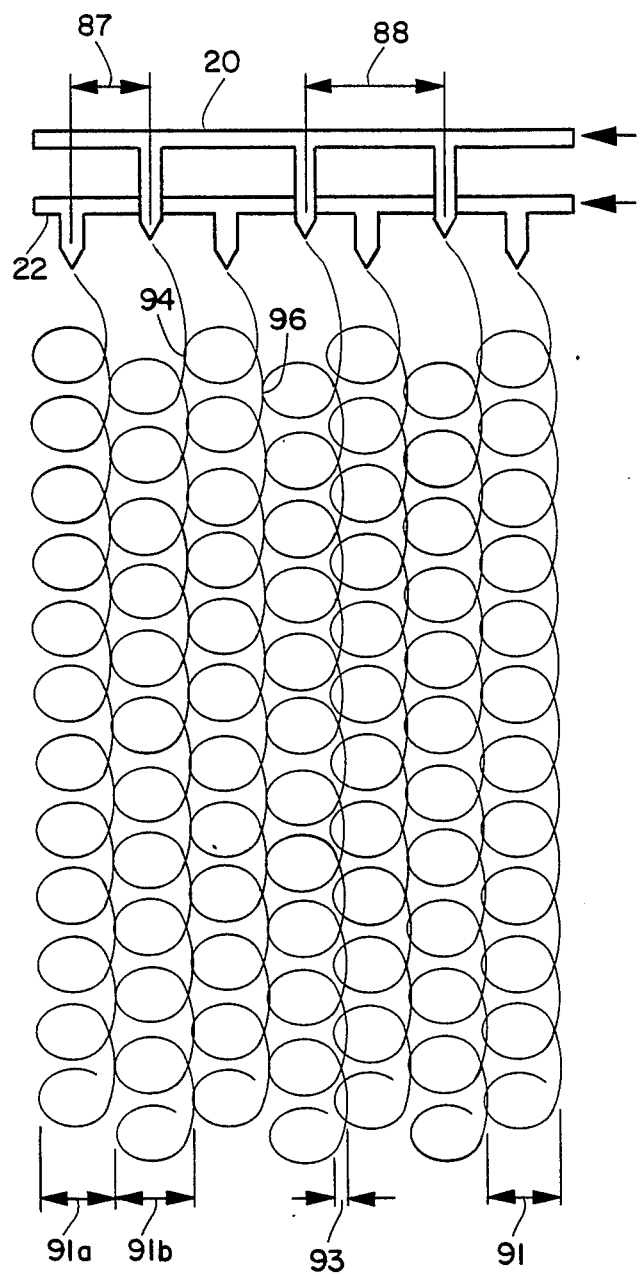
FIG. 7 representatively shows a deposition array comprising a plurality of juxtaposed, semi-cycloidal patterns.

It has also been found that the size and diameter of the deposition pattern can be effectively regulated by controlling the dimensions of chamber 81. In particular, the rate of radial expansion of the path of the swirling adhesive stream can be adjusted by selectively increasing or decreasing the axial length dimension 75 of chamber 81. For a given distance between nozzle unit 24 and web 14, increasing the axial length dimension reduces the rate of expansion and produces a deposition pattern having a relatively narrower width 91 (FIG. 7). Decreasing the axial dimension increases the rate of expansion and produces a deposition pattern having a relatively greater width. With the shown embodiment of the invention, for example, the axial length 75 of flange member 79, and thus the axial length of chamber 81, is adjusted to be within the range of about 0.076–0.10 cm. to expand the path of the adhesive stream at a rate sufficient to allow placement of web 14 at a distance of about 2.5–3.5 cm. from the exit of orifice 82 in nozzle unit 24, while still providing a deposited adhesive pattern width 91 of at least about 1.2 cm.

The length of chamber 81 can also affect the ability of the system to tolerate start-up conditions. In particular, during start-up, there is relatively more air and relatively less adhesive than during normal running conditions. If the chamber is too long (the axial dimension 75 is too great), excessive amounts of adhesive may accumulate on the nozzle unit during start-up and interfere with the formation of desired adhesive deposition patterns, such as the formation of substantially uniform adhesive patterns.

During the operation of a representative system, the selected hot-melt adhesive is heated to its molten state and supplied from a conventional reservoir. Suitable adhesives include, for example, 34-5522 or 34-5510 adhesive supplied by National Starch and Chemical Corp., and other hot-melt adhesives having equivalent properties. The adhesive is heated to a temperature sufficient to allow the molten adhesive to be pumped and extruded through the nozzle units. In the illustrated embodiment, the hot-melt adhesive is heated to a temperature of about 275–400° F. (about 135–204° C.), and the molten adhesive is metered and pumped through suitable conduits and delivered to transfer plate 44.

Figure 8:
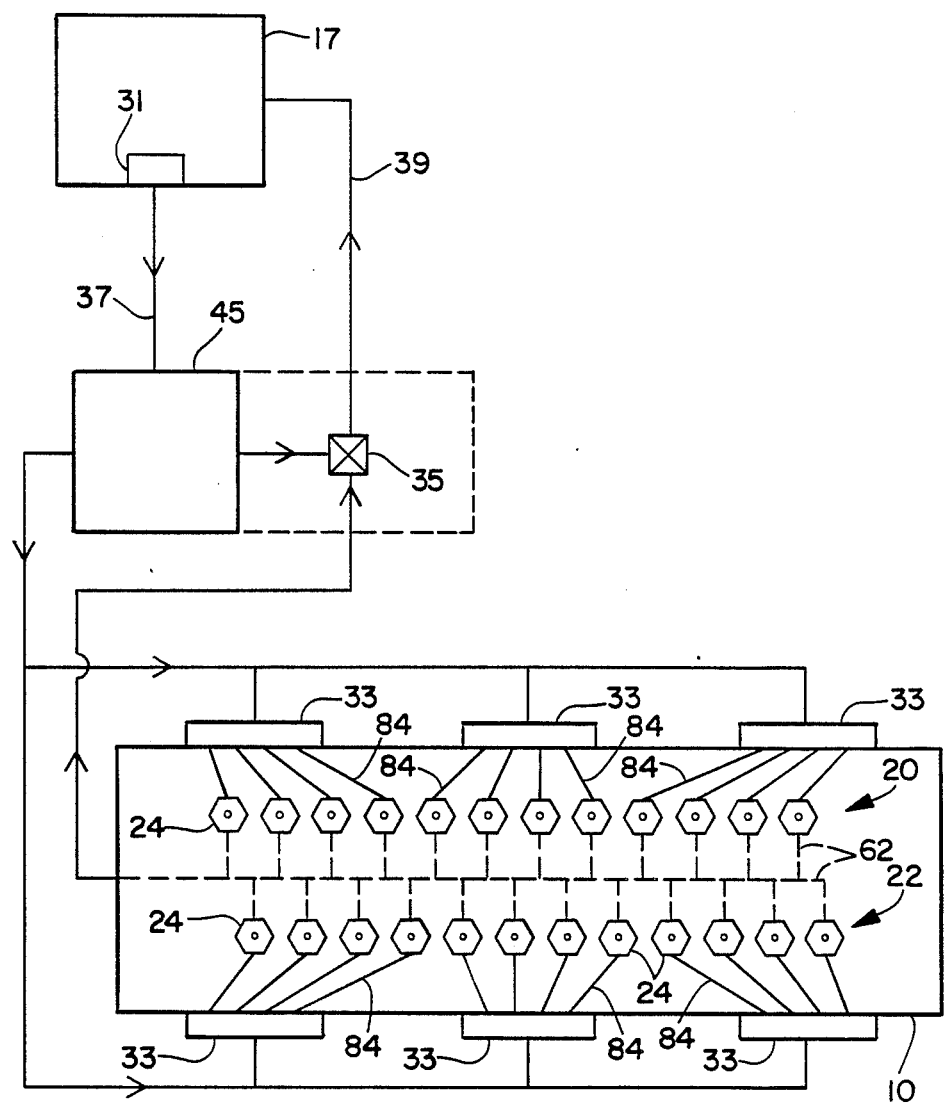
FIG. 8 shows a schematic representation of the adhesive delivery system.

Referring to FIG. 8, a conventional single-stream metering pump 31 delivers molten adhesive from a reservoir tank 17 through supply line 37 to a common manifold 45 located at nozzle assembly 10. Pump 31 is suitably sized and configured to supply and pressurize the adhesive held in manifold 45. Excess pressure in manifold 45 is released through pressure relief valve 35, which directs and recirculates the released adhesive through adhesive return line 39 back to the reservoir tank. In the shown embodiment, the relief valve is adjusted to maintain in manifold 45 an adhesive pressure which is within the range of about 10-35 psi.

A plurality of conventional pumps draw molten adhesive from manifold 45, and deliver individual metered streams of adhesive to each nozzle unit 24. The shown embodiment of the invention employs a plurality of multistream metering pumps 33, which are configured to deliver individual selected amounts of molten adhesive at predetermined rates to the nozzle units. More particularly, each multistream metering pump 33 can be a commercially available, four-stream metering pump which is capable of delivering precisely measured amounts of adhesive through independent porting and conduits to transfer plate 44, and then through independent conduits 84 to four individual nozzle units. For example, the shown embodiment of the invention employs six, four-stream metering pumps 33 to supply molten adhesive to two nozzle banks 20, 22, wherein each nozzle bank comprises twelve individual nozzle units 24. It is readily apparent, however, that additional metering pumps could be employed to supply adhesive to additional nozzle units. Also, different size metering pumps 33 could be employed configured to deliver greater or less than four metered streams from each pump. Any such changes or modifications are contemplated as being within the scope of the invention.

If one or more of the metered streams of adhesive goes to a nozzle location which has been closed with a plug 100 (FIG. 5), adhesive will travel through return ports 62, through transfer plate 44 into manifold 45, and then recirculate to reservoir 17. Similarly, if a nozzle unit should become plugged, the nozzle unit includes a mechanism for venting excess pressure and adhesive through adhesive return ports 62.

The configuration of the invention can advantageously provide a substantially uniform and substantially equalized flow of adhesive from each of the nozzle units. The invention can also provide a more precise control of the adhesive deposition patterns onto the chosen substrate. In one aspect of the invention, the flow rate of adhesive from each of the nozzle units can be regulated to have a variation of not more than about plus or minus 5%. In further aspects of the invention, the adhesive flow rate is preferably controlled to have a variation of not more than about plus or minus 2%, and more preferably, is controlled to have a variation of not more than about plus or minus 1% to provide improved performance. Thus, the invention can produce a more uniform array of adhesive deposition patterns over the surface of the substrate, and the resultant, more uniform distribution of adhesive add-on can thereby produce more uniform bonding of the final product with improved product integrity.

Suitable metering pumps for use with the invention are manufactured by various commercial vendors. The four-stream metering pump 33 can, for example, comprise an Acumeter MBE-HA manifold pump coupled to a #15747 front-pump mechanism and a #15668 drive-pump mechanism. The various pump mechanisms can be connected to an Acumeter assembly which provides a manifold for incoming adhesive and provides a distribution system for the individual streams of adhesive metered from the pump mechanisms. Acumeter, Inc. is a company having facilities in Marlborough, Mass.

In the illustrated embodiment, metering pumps 33 deliver hot-melt adhesive to the transfer plate at a pressure of about 250–500 psi. The liquid hot-melt adhesive flows from the metering pumps into transfer plate 44 through porting located in manifold 45 and then through passages 84 into nozzle plate 32, where the adhesive is introduced into the individual bore holes 48. From bore 48, the molten adhesive flows into supply passage 64 and proceeds through nozzle body 50 into orifice passage 82 of head button 80. The molten adhesive is then expelled through the individual nozzle units 24 in a generally continuous stream. In a particular aspect of the invention, the molten adhesive is delivered from each nozzle unit at a flow rate of about 2–20 gm./min. Preferably, the molten adhesive is delivered at a rate of about 9–15 gm./min., and more preferably is delivered at a rate of about 12.3 gm./min. to provide an improved deposition pattern.

To provide improved process control, FIG. 3 representatively shows an embodiment in which nozzle plate 32 is heated with a suitable heating mechanism 34, such as a Model E1078 heater produced by Acumeter, Inc. The heater is adjusted to maintain the nozzle plate at a temperature of about 270–400° F. (about 132–204° C.), and more preferably is maintained at a temperature within the range of about 290–320° F. (about 143–160° C.) to provide improved processing. A conventional thermostat 29 can be employed to help regulate the temperature. Since the nozzle plate is in close contact with transfer plate 44 and nozzle units 24, it will be readily apparent that heater 34 can operably heat the transfer plate and nozzle units, as well as the nozzle plate. While the shown embodiment incorporates three heaters 34, other numbers of individual heating units may also be employed.

As the hot-melt adhesive is extruded from the nozzle units, heated air is introduced into transfer plate 44 through gas inlet 36 (FIG. 3) from a conventional supply 19 (FIG. 9) of pressurized air. A suitable device 41 for heating the air is a Model GCH-1XT manufactured by Chromalox located in Ogden, Utah. In the illustrated embodiment of the invention, the air is heated to a temperature of about 250–400° F. (about 121–204° C.), and preferably is heated to a temperature of about 290–320° F. (about 143–160° C.) to provide improved process control. The heated air is conducted into nozzle plate 32 and delivered to gas inlet port 68, as shown in FIG. 4. From the gas inlet port, the heated air passes through the expanded region 70 of bore 48 and then into gas passage 74, through which the air is introduced into the space defined by groove 76. The air then passes through the group of angled gas jets 30, which direct the gas into a plurality of airstreams with each airstream having both a circumferential velocity component and an axial velocity component. The resultant group of airstreams operably engages and entrains the stream of molten adhesive issuing forth from the exit of orifice passage 82, and operably imparts a generally circular component of motion to the liquid adhesive stream. In a particular aspect of the invention, the airstreams are configured to cooperate and operably entrain the adhesive stream without excessively disrupting its substantially continuous, filamentary configuration. Consequently, as the molten adhesive moves toward substrate web 14, the adhesive stream traverses along a generally spiral or helical path having both a circumferential as well as an axial component of motion.

With reference again to FIG. 1, the invention is configured to move substrate web 14 at a selected speed along a predetermined machine direction 27 of the apparatus. As a result, the adhesive stream can be deposited onto web 14 in a curvilinear pattern. The deposited pattern of adhesive can be adjusted by regulating the movement speed of web 14, by regulating the circumferential and axial velocity components imparted to the adhesive stream, and by adjusting the distance between nozzle head button 80 and web 14.

The technique of the present invention includes suitable driving means, such as electric motors (not shown), for rotating the conveyor rollers at a speed sufficient to impart a desired transporting speed to web 14. High web speeds are desired to improve manufacturing efficiency, but at high web speeds, conventional adhesive spraying systems have not been able to maintain satisfactory control over the adhesive deposition patterns. In contrast to such conventional techniques, the method and apparatus of the present invention can produce accurate adhesive deposition patterns at web speeds of at least about 350 ft./min. In further aspects of the invention, sufficiently accurate and precise control of the deposition patterns can advantageously be maintained at web speeds of at least about 450 ft./min. and even at web speeds of at least about 600 ft./min. The shown embodiment may, for example, provide a web speed of about 800 ft./min. and may further provide a web speed of up to about 1,000 ft./min.

Figure 6:
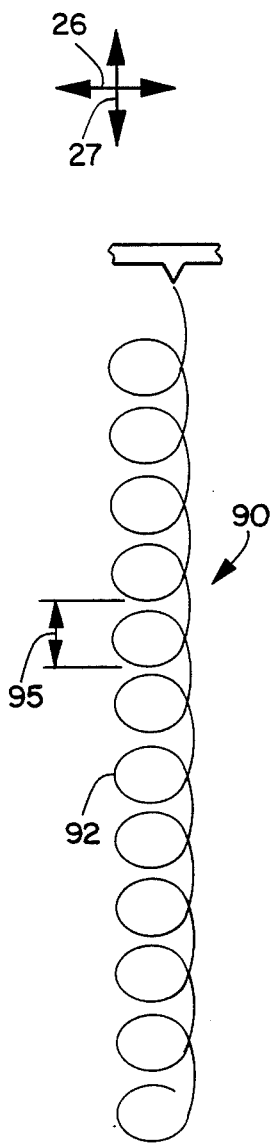
FIG. 6 representatively shows a deposition array comprising a semi-cycloidal pattern.

In a particular aspect of the invention, the method and apparatus can be adjusted to deposit each individual stream of hot-melt adhesive into a looping, semi-cycloidal pattern. In the general sense, a cycloid is the path traced by a point on the peripheral circumference of a wheel as the wheel rolls over a flat surface without slippage. If, however, there is slippage between the surface and the rolling wheel, the point on the circumference of the wheel will trace a path having a retroceding section which forms a loop in the traced path. The semi-cycloidal pattern representatively shown in FIG. 6 is similar in form to the path traced by the point on the wheel where the wheel is rolling with slippage. As a result, each semi-cycloidal pattern has a retroceding loop section 92 traced by the deposited hot-melt adhesive.

It has been discovered that a generally continuous, semi-cycloidal pattern of adhesive can be produced by suitably controlling the air pressure supplied to the angled gas jets 30 within the individual nozzle units. Accordingly, a particular aspect of the invention includes a gas pressure regulator 18, such as a Model R11 manufactured by C. A. Norgren Co. having facilities in Littleton, Colo. The pressure regulator is constructed and arranged to deliver about 10–40 psi of air pressure, and preferably is configured to provide about 15–25 psi of air pressure to the nozzle units. In the illustrated embodiment of the invention, too low an air pressure, such as a pressure below 15 psi, will not produce the desired loop deposition pattern at the selected adhesive throughput rate. Instead, the pattern will have the appearance of a wavy line and can provide inadequate distribution and coverage of adhesive over the surface area of the substrate. If the supplied air pressure is too high, the deposited pattern of adhesive may suitably cover the surface of the web, but the airstreams can excessively scatter the positioning of the adhesive. As a result, the cross-directional positioning of the adhesive will be inaccurate and there can be excessive overspray which would contaminate the equipment and waste adhesive.

Figure 9:
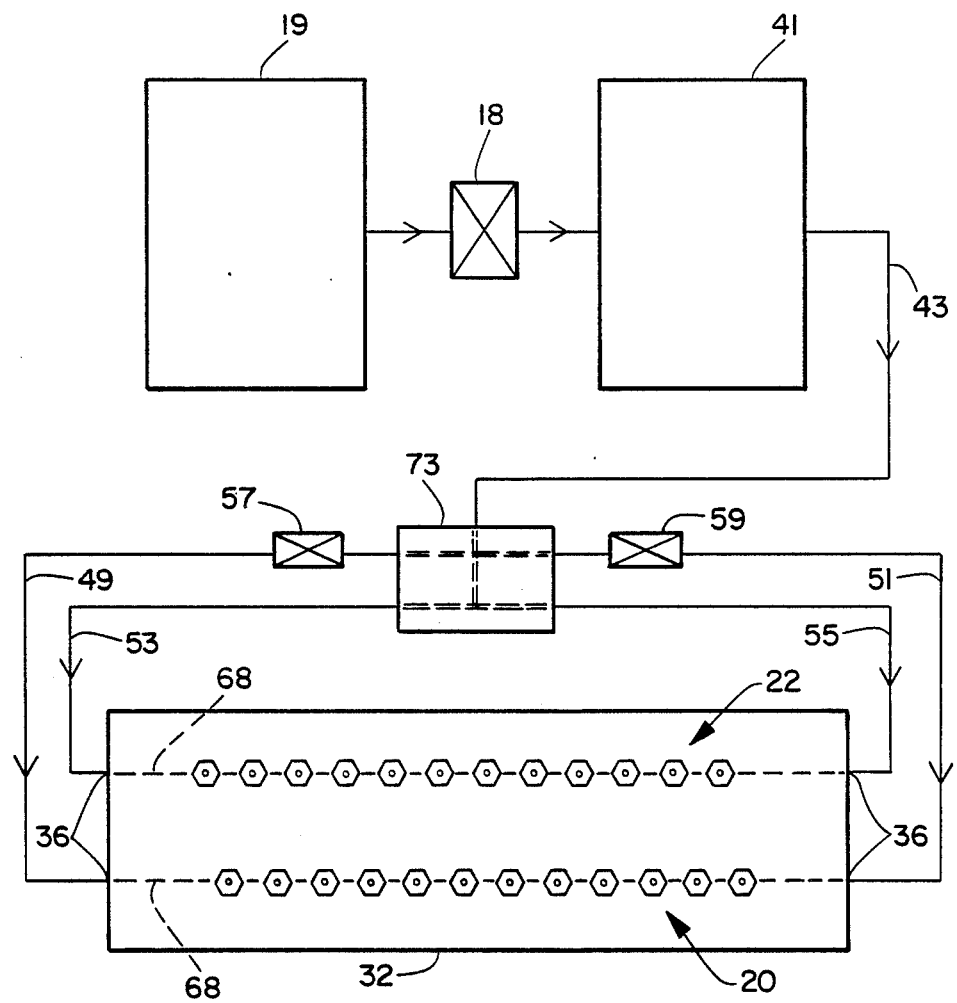
FIG. 9 shows a schematic representation of the heated air delivery system.

A particular aspect of the invention can include separate, gas pressure regulators for nozzle banks 20 and 22, as representatively shown in FIG. 9. Such an arrangement may be especially useful when the individual nozzle banks have unequal numbers of nozzle units 24. For example, first nozzle bank 20 may have thirteen nozzle units, and second nozzle bank 22 may have twelve nozzle units. In such a situation, the separate gas flow regulators may be adjusted to supply different amounts of gas to the different nozzle banks. More particularly, less gas could be supplied to the nozzle bank having fewer nozzle units to fine tune the system.

In the embodiment shown in FIG. 9, air or other suitable gas is delivered from a designated gas supply 19 through control valve 18 into gas heater 41. The heated air then travels through an insulated supply line 43 to a distribution manifold 73 which splits the heated air into four individual air streams. Two air streams are directed to nozzle plate 32 through air conduits 49 and 51 to supply heated air to nozzle bank 20. Two other air streams are directed to the nozzle plate through air conduits 53 and 55 to supply heated air to second nozzle bank 22. Gas flow control valves 57 and 59 are constructed and arranged to regulate the flow of heated air through conduits 49 and 51, respectively.

It has also been discovered that the distance between nozzle units 24 and web 14 is an important parameter for providing the desired semi-cycloidal deposition pattern. Accordingly, in one aspect of the invention, the distance between the exits from nozzle passages 82 and the position of web 14, as it moves over rollers 16, is limited to a maximum separation distance 98 (FIG. 1A) of about 2 in. Preferably, the separation distance is not more than about 1.75 in., and more preferably, the separation distance is within the range of about 1.0–1.5 in. to provide improved control over the deposition patterns. The reduced separation distance, for example, can reduce the chances of disrupting the desired deposition patterns with extraneous side currents of air or other windage.

With the shown embodiment of the invention, the semi-cycloidal pattern from each nozzle has a cross-directional extent or width 91 (FIG. 7) of about 0.5–0.75 in. (about 1.27–1.9 cm.). In addition, the individual spacing 95 between adjacent loops of the adhesive pattern, as measured along the machine direction, is within the range of about 0.5–2.0 cm. Preferably, the machine direction spacing between loops is about 0.7–1.4 cm., and more preferably is about 0.8–1.0 cm. to provide improved bonding characteristics. If the spacing is too small, an excessive amount of adhesive will be expended, and if the spacing is too great, the adhesive pattern may provide inadequate bonding strength.

In one aspect of the invention, the method and apparatus are constructed and arranged to form an array composed of a plurality of juxtaposed, semi-cycloidal patterns of hot-melt adhesive, as representatively shown in FIG. 7. In a further aspect of the invention, the juxtaposed semi-cycloidal patterns are arrayed in a configuration wherein two or more adjacently located, semi-cycloidal patterns contact each other along adjacent marginal side sections 94, 96 thereof. For example, the adjacently located patterns of hot-melt adhesive may contact each other along a substantially continuous line which extends along machine direction 27 of web 14. Accordingly, the plurality of semi-cycloidal patterns illustrated in FIG. 7 contact one another along substantially continuous, generally parallel lines which extend along the longitudinal, machine direction 27.

To produce the desired array of adhesive patterns on web 14, a plurality of nozzle units are selectively positioned along the cross-direction 26 of the apparatus. More specifically, the incorporation of each additional nozzle unit can effectively add another semi-cycloidal pattern of adhesive and thereby incrementally increase the cross-directional width of web 14 which is covered with adhesive.

It has, however, been discovered that a conventional, linear arrangement of the individual nozzle units 24 along cross-direction 26 may not produce the desired deposition array of adhesive. It has been found that the group of airstreams issuing forth from one nozzle unit 24 would excessively interfere with the group of airstreams issuing forth from an adjacent nozzle unit As a result, the desired array of juxtaposed semi-cycloidal patterns can be disrupted and the bonding effectiveness can be excessively reduced.

One technique for addressing this problem has been to increase the cross-directional spacing between adjacent nozzle units. Such a technique, however, can leave undesirable gap regions between adjacent patterns of deposited adhesive The gap regions would then be unbonded to the completed assembly, and would have lower strength and poorer integrity.

The structure and arrangement of the present invention provides an improved configuration which more effectively reduces the interaction between adjacent groups of airstreams and more effectively reduces the interference between adjacent streams of adhesive. In particular, the invention can be advantageously configured with the nozzle units 24 arranged in the alternating, offset and staggered arrangement previously discussed with reference to FIG. 2. As representatively shown in FIG. 2, the individual nozzle units 24 are grouped into a first nozzle bank 20 and a second nozzle bank 22. Within first nozzle bank 20, for example, the adjacent nozzle units 24a and 24b are spaced apart by a cross-directional distance which is sufficient to substantially prevent adjacent groups of airstreams from interfering with each other, and also to substantially prevent adjacent swirling streams of hot-melt adhesive from interfering with each other as they traverse from the nozzle units to the web substrate. Accordingly, the cross-directional separation 88 between adjacent nozzle units 24a and 24b should be not less than about the average of the widths 91a, 91b (FIG. 7) of the associated, adjacent semi-cycloidal patterns produced by these nozzle units. In the shown embodiment, the cross-directional spacing between nozzle units 24a and 24b is approximately equal to two times the width 91 of one of the semi-cycloidal patterns 90. FIG. 2 representatively shows a particular nozzle bank having individual nozzle units 24 which are substantially equally spaced along the cross-direction, but an unequal cross-directional spacing between adjacent nozzle units could also be employed.

The configuration of second nozzle bank 22 is similar to the configuration of first nozzle bank 20. The second nozzle bank, however, is offset from the first nozzle bank along the machine direction by an offset distance 23 sufficient to substantially prevent the airstreams from the first nozzle bank from interfering with the airstreams from the second nozzle bank, and to substantially prevent the motions of the adhesive streams from the first nozzle bank from interfering with the motion of the adhesive streams produced by the second nozzle bank. In the illustrated embodiment, the machine direction offset 23 is at least about 3.0 cm., and preferably is at least about 4.0 cm. to provide improved performance.

In addition to being offset in the machine direction, the nozzle units in second nozzle bank 22 are staggered in the cross-direction relative to the nozzle units in first nozzle bank 20. As can be seen in FIG. 2, the individual nozzle units comprising second nozzle bank 22 are positioned in the cross-directional gaps which separate the individual nozzle units comprising first nozzle bank 20. As a result, the nozzle banks 20, 22 in combination can provide a substantially complete coverage of adhesive over web 14 while substantially preventing undesired interaction or interference between the air streams and adhesive streams produced by the individual nozzle units 24. The invention can thereby advantageously provide a consistent deposition pattern from each of the nozzle units 24, and can provide a more accurate cross-directional positioning of the adhesive patterns on web 14. In one aspect of the lateral side edge 94 of one or more of the semi-cycloidal adhesive patterns 90 has a cross-directional variation of not more than about plus or minus 0.125 in. relative to a predetermined desired position along the cross-direction. Preferably, the cross-directional positioning variation is not more than about plus or minus 0.063 in., and more preferably is not more than about plus or minus 0.032 in. to provide improved performance.

The offset and staggered relationship between first nozzle bank 20 and second nozzle bank 22 can also provide the capability to selectively adjust an amount of overlap 93 (FIG. 7) between adjacent, semi-cycloidal patterns of adhesive. For example, the individual nozzle units within first nozzle bank 20 can have substantially equal cross-directional separations 88 which are between about 1-2 times an average pattern width 91. The individual nozzle units within second nozzle bank 22 can then be configured with similar cross-directional separations, and the second nozzle bank can be offset in the machine direction from the first nozzle bank. In addition, the nozzle units within second nozzle bank 22 can be staggered with respect to the nozzle units within first nozzle bank 20. The stagger 87 distance, for example, can be adjusted to be about one-half of separation distance 88, and the apparatus can be arranged to have the nozzle units produce adhesive patterns of substantially equal width 91. As a result of this particular configuration, the apparatus can produce an array of multiple, semi-cycloidal adhesive patterns wherein the adjacent patterns overlap by a discrete distance 93. For example, a particular aspect of the invention provides an overlap distance 93 within the range of about 0.125-0.25 in. (about 0.32-0.63 cm.) to thereby produce a desired combination of good bonding strength and economy of adhesive add-on.

The illustrated embodiment of the invention representatively shows a configuration wherein the nozzle units that respectively form immediately adjacent deposition patterns are arranged in a substantially "zig-zag" layout. In an alternative embodiment of the invention, the desired offset and staggered arrangement of the individual nozzle units may be accomplished by positioning three or more nozzle units substantially along a line which extends diagonally across the machine-cross direction. A nozzle bank having such a construction could be rotated to adjust the angle of the diagonal to control the amount of overlap 93 between adjacent deposition patterns 91.

Another advantage afforded by the present invention is an ability to incrementally reduce the total width of the area covered by the array of deposited adhesive patterns. More particularly, the total width of the web area, which is occupied by the deposited adhesive can be adjusted by selectively removing nozzle units and capping off the corresponding, associated bore holes 48 with a plug mechanism 100.

Figure 5:
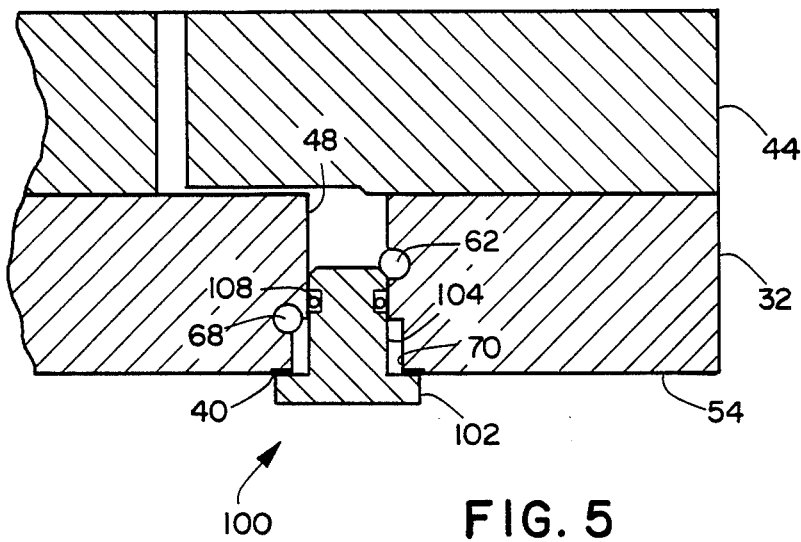
FIG. 5 representatively shows a cross-sectional view of a plug assembly employed to adjust the deposition width and pattern provided by the present invention.

As representatively shown in FIG. 5, plug 100 is substantially cylindrical in shape and includes an annular flange 102 formed at one end thereof. Flange 102 is constructed and arranged to sealingly engage surface 54 of nozzle plate 32 and to effectively cover the opening of the bore hole 48. Gasket member 40 provides a substantially airtight seal between surface 54 and flange 102. The gasket is composed of a conventional fibrous gasket material, and is configured to reduce air leaks caused by irregularities in the mating surfaces. A cylindrical body section 104 of the plug extends into bore 48 and includes a circular groove configured to accommodate therein a sealing means, such as O-ring 108. O-ring 108 is positioned between adhesive return port 62 and the expanded region 70 of bore hole 48. In addition, the axial length of plug body 104 is selected so as to stop short of the position of adhesive return port 62. As a result, hot-melt adhesive is able to recirculate from bore 48 through adhesive return port 62 and return to a suitable reservoir accumulator.

In a further aspect of the invention, the method and apparatus include a pressure release means for relieving excessive pressure built up behind a partially or completely plugged nozzle orifice. Referring to FIG. 4, O-ring 61 is constructed and arranged to bypass excessive pressure which might build up behind a plugged nozzle orifice. In particular, O-ring 61 is constructed and arranged to operably deflect to allow the passage of pressurized adhesive from bore hole 48 past the position of O-ring 61 and into adhesive return port 62. In the illustrated embodiment, O-ring 61 is constructed to operably deflect when subjected to an adhesive pressure of more than about 1400 psi. As a result of the configuration of O-ring 61 and the positioning of adhesive return port 62, the invention can substantially prevent the undesired backing of adhesive into the air system comprising expanded section 70 and gas inlet port 68. The distinctive configuration of the invention can thereby reduce unanticipated maintenance of the system.

The present invention can be employed to produce distinctive manufactured articles, such as disposable garments, infant diapers, feminine care products, incontinence products and other adhesively bonded assemblies. More particularly, the present invention can be employed to produce distinctive absorbent articles, such as disposable diaper 110.

Figure 10:
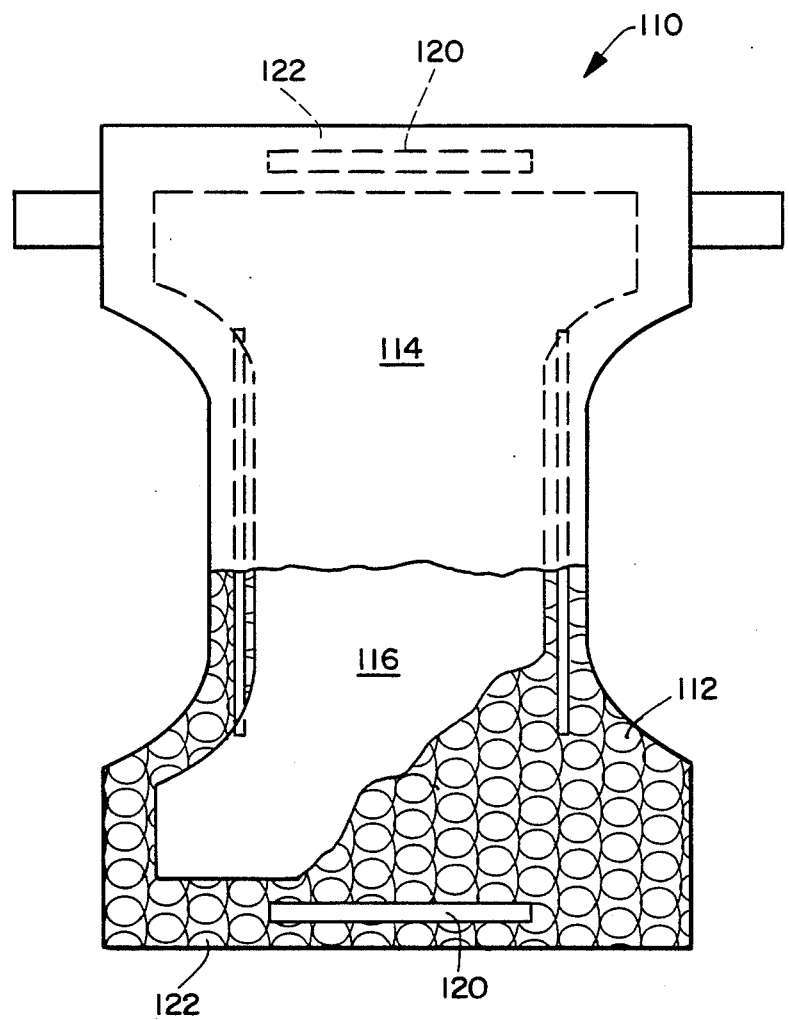
FIG. 10 representatively shows a disposable diaper constructed in accordance with the present invention.

With reference to FIG. 10, disposable diaper 110 includes an outer layer 112, a bodyside layer 114 and an absorbent body 116 sandwiched between the outer and bodyside layers. The outer and bodyside layers extend outwardly past the side edges of absorbent body 116 to form side seals and side flaps or cuffs, which are constructed to contact and sealingly engage the thighs of the wearer. In certain arrangements, leg elastics are positioned in the side flaps to produce elasticized gathers, which can provide improved sealing and leakage prevention around the wearer's legs and improved fit. In addition, the outer and bodyside layers may extend beyond the longitudinal edges of absorbent body 116 to form waistband portions of the diaper, and waist elastics 120 may be assembled into the waist band portions. Absorbent body 116 may comprise one or more layers of high wet-strength tissue wrapped around an absorbent core composed of a mixture of woodpulp fluff and superabsorbent particles. A representative diaper article is described in U.S. Pat. No. 4,699,823 issued Oct. 13, 1987 to S. Kellenberger, et al., which is hereby incorporated by reference to the extent it is consistent with the present disclosure.

Diaper 110 includes an array of adhesive arranged to secure one or more of the layers to the absorbent body. The adhesive array is distinctively composed of a plurality of juxtaposed, semi-cycloidal patterns of adhesive which extend substantially along a longitudinal dimension of the article. For example, outer layer 112 may be secured to absorbent body 116 by the array of semi-cycloidal patterns of adhesive. Alternatively, the array of adhesive may be employed to secure bodyside layer 114 to the absorbent body. Similarly, the array of adhesive may operably secure outer layer 112 to bodyside layer 114, or secure the tissue wrap to the absorbent core. In the illustrated embodiment, an adhesive array composed of a plurality of juxtaposed, semi-cycloidal patterns of adhesive is applied with the adhesive patterns extending substantially along the lengthwise dimension of the article. In addition, the adjacent patterns of the adhesive contact each other along adjacent, marginal side portions of the semi-cycloidal patterns. The shown embodiment of diaper 110 includes adjacent patterns of adhesive which contact each other along substantially continuous, generally parallel lines which extend along the longitudinal dimension. Alternatively, the adjacent semi-cycloidal patterns may overlap each other along the side margins of the individual patterns.

The amount of adhesive distributed over outer layer 114 is within the range of about 1.0–6.0 gm. per square meter. Preferably, the amount of adhesive add-on is within the range of about 4.0–5.0 gm. per square meter to provide more improved efficiency. When compared to the amount of adhesive add-on employed with construction adhesive applied in the pattern of generally linear, parallel lines of adhesive, the amount of adhesive incorporated into the distinctive patterned array of the invention can be decreased to about 50% of the conventional amount of adhesive. Even though the amount of adhesive employed is reduced, the distinctive adhesive distribution provided by the present invention can adequately maintain the integrity of the final product. In particular, when compared to the conventional, parallel adhesive line construction technique, the bonding strength at end seal region 122 can be substantially maintained even though the amount of adhesive add-on is reduced. For example, the amount of adhesive may be reduced from about 0.94 gm./diaper to about 0.54 gm./diaper and still maintain approximately the same end seal strength. In addition, the distribution of the adhesive in the distinctive patterns and arrays of the invention can advantageously provide a more flexible outer cover layer which has a more pleasing cloth-like appearance and feel.

Figure 11:
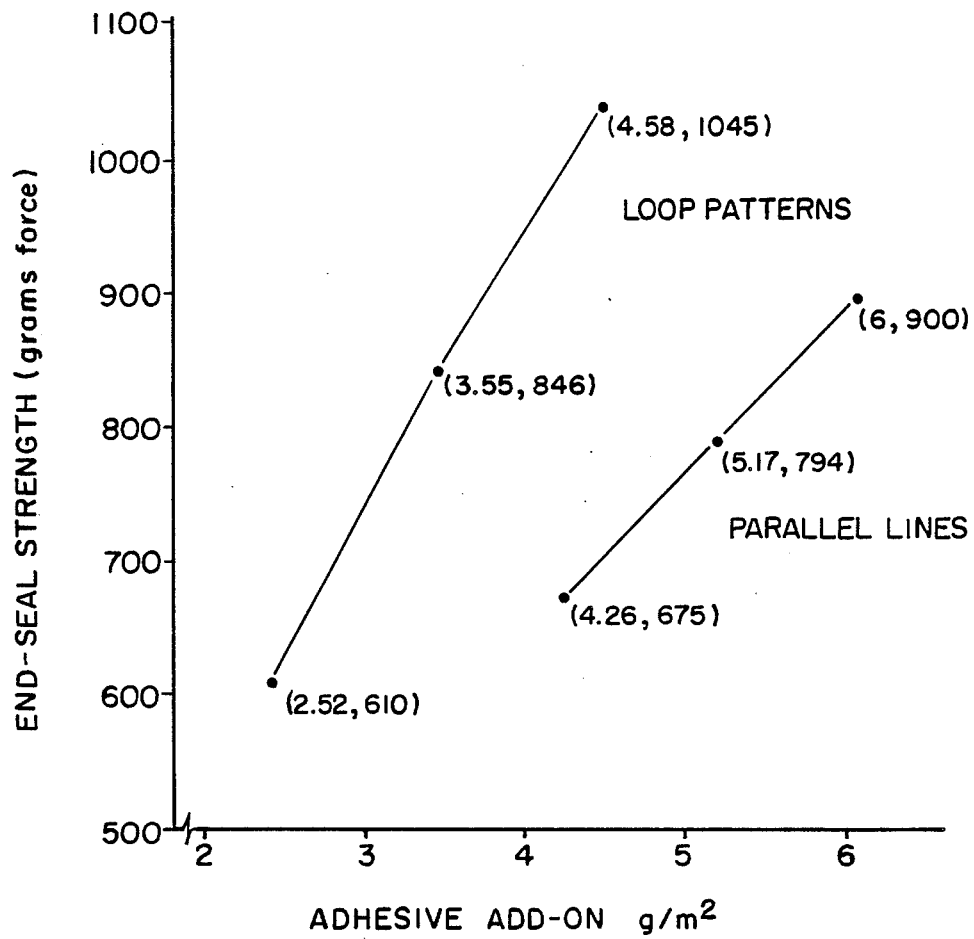
FIG. 11 representatively shows a graphic comparison of end seal strengths provided by conventional bead-lines of adhesive and by the adhesive patterns of the present invention.

A representative comparison of the end seal strengths and the amount of adhesive add-on is set forth in the graph shown in FIG. 11. The graph representatively shows data generated from medium-size disposable diapers, constructed with a conventional hot-melt construction adhesive. More particularly, the diapers were constructed with National Starch 34-5522 or 34-5510 adhesive. When compared to conventional, generally parallel adhesive lines, the looping-type adhesive patterns produced in accordance with the present invention can advantageously provide increased end-seal strengths at the same amounts of adhesive add-on. Alternatively, the adhesive patterns produced in accordance with the present invention can advantageously provide the same end-seal strengths with lower amounts of adhesive add-on.

For the purposes of the present invention, the following procedure is a suitable technique for determining the end seal strength:

A test specimen is prepared by cutting a rectangular sample measuring 3 in.×5 in. from the center of the waistband section of the diaper. One 3 in. side of the sample corresponds to the terminal waistband edge, and the two 5 in. sides extend along the longitudinal length of the diaper. The fluff pad material is then removed from the sample without disturbing the patterns of adhesive in the end seal region of the sample. The end seal region is the portion of the sample wherein the bodyside liner is adhesively bonded or otherwise attached and laminated with the outer cover layer. The end seal strength corresponds to the force required to peel apart the bond between the liner and outer cover, and is expressed in terms of peak load measured in grams (gramforce). The apparatus employed to measure the end seal strength is an Instron tensile tester with a 10 kilogram load cell, or equivalent tensile testing apparatus, in conjunction with a Microcon microprocessor apparatus. The Microcon device analyzes input data to provide, for example, load vs. elongation plots and Total Energy Absorption information from the test sample, and is distributed by Instron Corp. having facilities at Canton, Mass. The Instron tensile test apparatus is set with a cross-head speed of 10 inches per minute and a chart speed of 2 inches per minute. The jaw spacing of the Instron apparatus is set at 4 inches. The Microcon apparatus is initialized to the following set of conditions:
Initial sample length=4 inch (guage length)
Cross-head speed=250 mm/min.
Automatic return=10 inch
Print mode=peak load, break energy The test sample will have a generally "Y" configuration wherein the end seal portion corresponds to the base of the Y, the liner material corresponds to one arm of the Y, and the outer cover material corresponds to the second arm of the Y. The two arms of the sample are secured in the jaws of the Instron apparatus with the inside of the sample facing toward the front of the Instron apparatus and the outer cover material held in the moveable jaw. The line of separation between the outer cover material and the liner material is positioned approximately half way between the two jaws. The cross-head motion of the Instron machine is then started, and when the sample has been completely peeled apart, the highest average peel force applied to the test sample is recorded.

Having thus described the invention in rather full detail, it will be readily apparent that various changes and modifications may be made without departing from the spirit of the invention. All of such changes and modifications are contemplated as being within the scope of the invention, as defined by the subjoined claims.

We claim:

1. An apparatus for depositing a pattern of material onto a substrate, comprising:

a. a first nozzle bank and at least a second nozzle bank with the first nozzle bank offset a selected distance from said second nozzle bank along a substrate movement direction of the apparatus, wherein each nozzle bank includes a plurality of spaced-apart nozzles which are substantially aligned along a cross-direction of the apparatus, and wherein the nozzles of said first nozzle bank are positioned in a staggered arrangement relative to the nozzle of said second nozzle bank, each nozzle including an orifice for forming a stream of said material, and including a group of gas jets for forming a group of gas streams which have selected velocities and are arranged to entrain the stream of material from said orifice to impart a swirling motion to the material stream as it moves toward said substrate;

b. transport means for moving said substrate past said nozzle banks along said substrate movement direction; and c. regulating means for controlling the velocities of said groups of gas streams to direct each stream of material in a substantially helical path toward said substrate and deposit said material thereon to form a plurality of juxtaposed, semi-cycloidal patterns of said material on said substrate.

2. An apparatus as recited in claim 1, wherein said nozzle banks and said regulating means are constructed and arranged to produce said plurality of semi-cycloidal patterns of material on said substrate in a configuration wherein two or more adjacently located, semi-cycloidal patterns contact each other along adjacent marginal side portions thereof.

3. An apparatus as recited in claim 2, wherein said adjacently located patterns of material contact each other along a substantially continuous line which extends along the machine direction.

4. An apparatus as recited in claim 1, further comprising means for selectively routing excess supplied material to a reservoir.

5. An apparatus as recited in claim 1, wherein said regulating means is constructed and arranged to control a selected cross-directional position of an edge of one or more of said semi-cycloidal patterns with a variance of not more than about plus or minus 0.063 inch relative to said selected position along said cross-direction.

6. An apparatus as recited in claim 1, wherein said regulating means is constructed and arranged to control a selected cross-directional position of an edge of one or more of said semi-cycloidal patterns with a variance of not more than about plus or minus 0.032 inch relative to said selected position along said cross-direction.

7. An apparatus as recited in claim 1, wherein said regulating means comprises a metering pump for delivering selected amounts of said material to said nozzles at predetermined rates.

8. An apparatus as recited in claim 1, wherein said nozzles are constructed to form substantially continuous filaments of said materials.

9. An apparatus as recited in claim 1, wherein said regulating means is constructed to deliver about 10–40 psi of gas pressure to said nozzles.

10. An apparatus as recited in claim 1, wherein said regulating means is constructed to deliver about 15–25 psi of gas pressure to said nozzles.

11. An apparatus as recited in claim 1, wherein said gas directing means comprises gas jets inclined circumferentially relative to an axial dimension of said nozzles.

12. An apparatus as recited in claim 1, wherein said regulating means is constructed to control a selected cross-directional position of an edge of one or more of said semi-cycloidal patterns within a variance of not more than about plus or minus 0.125 inch relative to said selected position along said cross-direction.

13. An apparatus as recited in claim 12, wherein said nozzle banks are arranged with a stagger distance configured to deposit said patterns of material with a selected overlap distance.

14. An apparatus as recited in claim 12, wherein said nozzle banks are arranged with a stagger distance configured to deposit said patterns of material with an overlap distance within the range of about 0.125–0.25 inch (about 0.32–).63 cm).

15. An apparatus for depositing a pattern of material onto a substrate, comprising:
a first nozzle for supplying a first stream of a selected viscous material;
a second nozzle for supplying at least a second stream of a selected viscous material, said second nozzle located in a position which is offset from said first nozzle along a substrate movement direction of said apparatus and staggered from said first nozzle along a cross-direction of said apparatus;
gas directing means for forming a plurality of gas streams, which have selected velocities and are arranged to entrain said first and second material streams to impart a swirling motion to each of the material streams as it moves toward said substrate;
transport means for moving said substrate past said nozzles along said substrate movement direction; and
regulating means for controlling said material streams and said gas streams to direct each of said material streams in a selected path toward said substrate and deposit said material thereon to form adjacent semi-cycloidal patterns of said material on said substrate.

16. An apparatus as recited in claim 15, wherein said regulating means is constructed and arranged to control a selected cross-directional position of an edge of one or more of said semi-cycloidal patterns with a variance of not more than about plus or minus 0.063 inch relative to said selected position along said cross-direction.

17. An apparatus as recited in claim 15, wherein said regulating means is constructed and arranged to control a selected cross-directional position of an edge of one or more of said semi-cycloidal patterns with a variance of not more than about plus or minus 0.032 inch relative to said selected position along said cross-direction.

18. An apparatus as recited in claim 15, wherein said regulating means comprises a metering pump for delivering selected amounts of said material to said nozzles at predetermined rates.

19. An apparatus as recited in claim 15, wherein said nozzles are constructed to form substantially continuous filaments of said materials.

20. An apparatus as recited in claim 15, wherein said regulating means is constructed to deliver about 10–40 psi of gas pressure to said nozzles.

21. An apparatus as recited in claim 15, wherein said regulating means is constructed to deliver about 15–25 psi of gas pressure to said nozzles.

22. An apparatus as recited in claim 15, wherein said gas directing means comprises gas jets inclined circumferentially relative to an axial dimension of said nozzles.

23. An apparatus as recited in claim 15, wherein said regulating means is constructed to provide a flow rate of viscous material from each of said nozzles with said flow rate having a variation of not more than about plus or minus 5%.

24. An apparatus as recited in claim 15, wherein said regulating means is constructed to provide a flow rate of about 2–20 gm/min of viscous material from each of said nozzles, with said flow rate having a variation of not more than about plus or minus 5%.

25. An apparatus as recited in claim 15, wherein each material stream is substantially continuous and wherein said gas directing means is constructed to impart a substantially circular, swirling motion to each of said material streams as it moves toward said substrate.

26. An apparatus as recited in claim 25, wherein said regulating means is constructed to direct each of said material streams along a substantially helical path toward said substrate.

27. An apparatus as recited in claim 15, wherein said regulating means is constructed and arranged to control a location of an edge of one or more of said semi-cycloidal patterns at a selected position along said cross-direction with a variance of not more than about plus or minus 0.125 inch relative to said selected cross-directional position.

28. An apparatus as recited in claim 27, wherein said nozzles are arranged with a stagger distance configured to deposit said patterns of material with a selected overlap distance.

29. An apparatus as recited in claim 17, wherein said nozzles are arranged with a stagger distance configured to deposit said patterns of material with an overlap distance within the range of about 0.125–0.25 inch (about 0.32–0.63 cm).

* * * * *